(12) United States Patent
Holstein (10) Patent No.: US 8,336,712 B2
(45) Date of Patent: Dec. 25, 2012

(54) DEVICES AND SYSTEMS FOR PROVIDING INCREASED ACCESS TO FIRST AID SUPPLIES

(76) Inventor: Michael Holstein, Clearwater, FL (US)

( * ) Notice: Subject to any disclaimer, the term of this patent is extended or adjusted under 35 U.S.C. 154(b) by 0 days.

(21) Appl. No.: 13/109,908

(22) Filed: May 17, 2011

(65) Prior Publication Data

US 2012/0292216 A1 Nov. 22, 2012

(51) Int. Cl.
*A61F 13/00* (2006.01)
*G07F 11/00* (2006.01)
(52) U.S. Cl. ......................... 206/441; 221/133
(58) Field of Classification Search ............... 206/440, 206/441; 221/25, 69, 70, 73, 139, 92, 133; 24/10 R, 30.5 R, 336, 561; 30/40.2
See application file for complete search history.

(56) References Cited

U.S. PATENT DOCUMENTS

| | | | | |
|---|---|---|---|---|
| 1,262,963 A | * | 4/1918 | McCrea | 206/440 |
| 2,523,804 A | * | 9/1950 | Albro | 24/10 R |
| 2,564,712 A | * | 8/1951 | Muros et al. | 30/40.2 |
| 3,217,967 A | * | 11/1965 | Jackson | 24/30.5 R |
| 3,231,076 A | * | 1/1966 | Freiman | 24/336 |
| 3,349,454 A | * | 10/1967 | Thomson | 24/561 |
| 4,194,624 A | * | 3/1980 | Spiegelberg | 206/441 |
| 4,563,832 A | * | 1/1986 | Drebot | 43/44.99 |
| 4,807,753 A | * | 2/1989 | Goldstein | 206/440 |
| 6,050,413 A | * | 4/2000 | Benedetti | 206/440 |
| 6,918,488 B2 | * | 7/2005 | Renhed | 206/440 |
| 7,017,744 B2 | * | 3/2006 | Persson | 206/440 |
| 7,644,818 B2 | | 1/2010 | Spoljaric | |
| 7,762,635 B2 | | 7/2010 | Spoljaric | |
| 2002/0162847 A1 | * | 11/2002 | Roy | 221/92 |

FOREIGN PATENT DOCUMENTS

| | | |
|---|---|---|
| WO | WO-2004-00688 A1 | 12/2003 |
| WO | WO-2006-78200 A1 | 7/2006 |
| WO | WO-2006-78201 A1 | 7/2006 |

* cited by examiner

*Primary Examiner* — Bryon Gehman
(74) *Attorney, Agent, or Firm* — Wilson, Sonsini, Goodrich & Rosati (57) ABSTRACT

Provided are systems, devices, dispensers, clips, and methods of using the same, for dispensing bandages comprising: a dispenser body defining an interior compartment and comprising a front wall with an exposed upper edge; a bandage pack disposed in the interior compartment; and a removable retaining clip adapted to reversibly interlock with the exposed upper edge of the front wall to retain a bandage pack in the dispenser body.

19 Claims, 6 Drawing Sheets

DEVICES AND SYSTEMS FOR PROVIDING INCREASED ACCESS TO FIRST AID SUPPLIES

BACKGROUND OF THE INVENTION

Medical emergencies pose a serious and prevalent threat to society. According to the Centers for Disease Control and Prevention (CDC), Americans suffered 29.6 million non-fatal injuries in 2009. Over 2 million of these non-fatal injuries were cuts or punctures. Emergency departments in the United States average approximately 400 visits for each 1000 people every year. The CDC further reports that injuries in the home result in about 30% of all injury-related emergency department visits. The National Institutes of Health and the Mayo Clinic recommend immediately covering wounds such as cuts, scrapes, and punctures with a sterile bandage.

SUMMARY OF THE INVENTION

Effective first aid requires easy and rapid access to sterile dressings appropriate to cover, protect, and help stop bleeding from a variety of wounds such as cuts, scrapes, and punctures. Dressings, such as bandages, should be readily available, clean, and dry. Moreover, bandages should be dispensed in a way that allows uncomplicated application with one hand. Because many injuries occur in the home, bandage dispensers should be attractive and appropriate for use in a home in a visible and easily accessed location. Accordingly, we have identified a long-felt and unmet need for a home bandage dispenser that includes a mechanism to retain a variety of bandage packs such that individual bandages are dispensed clean, dry, and ready to apply, yet is easily refilled.

In one aspect, disclosed herein are systems for dispensing bandages comprising: a dispenser body defining an interior compartment with an open or partially open top and comprising a front wall with an exposed upper edge and at least one interior compartment divider; at least one bandage pack disposed in said interior compartment, wherein said bandage pack comprises at least one individually wrapped bandage; and at least one retaining clip, wherein said clip retains a bandage pack in said dispenser body.

In some embodiments, the retaining clip fits over the exposed upper edge of the front wall of the dispenser body and reversibly interlocks with the dispenser body such that it allows removal of individual bandages from the interior compartment through the top of the dispenser body, but does not allow removal of a bandage pack disposed therein. In some embodiments, the interlocking between the retaining clip and the dispenser body results from interaction of a protrusion and a recess. In further embodiments, a protrusion is associated with the dispenser body and a recess is associated with a retaining clip. In other embodiments, a protrusion is associated with a retaining clip and a recess is associated with the dispenser body. In some embodiments, the interlocking between the retaining clip and the dispenser body results from friction. In some embodiments, the retaining clip interferes with removal of a bandage pack by fitting over the front wall of the dispenser body and a portion of a bandage pack simultaneously. In some embodiments, the system comprises 1-11 retaining clips. In further embodiments, the system comprises 3-9 retaining clips. In still further embodiments, the system comprises 6 retaining clips.

In some embodiments, a divider is planar and disposed in the interior compartment of the dispenser body perpendicular to said front wall. In some embodiments, a divider is fixed. In other embodiments, a divider is removable or repositionable.

In some embodiments, the dispenser body comprises from 1 to 10 dividers. In further embodiments, the dispenser body comprises from 3 to 7 dividers. In still further embodiments, the dispenser body comprises 5 dividers. In some embodiments, the system comprises one bandage pack for each division in the interior compartment and one retaining clip for each bandage pack.

In some embodiments, the dispenser body further comprises a rear wall with pre-drilled holes to facilitate mounting the dispenser to a fixed surface. In some embodiments, the dispenser body further comprises a rear wall with adhesive to facilitate mounting the dispenser to a fixed surface.

In some embodiments, the system comprises 1-11 bandage packs. In further embodiments, the system comprises 3-9 bandage packs. In still further embodiments, the system comprises 6 bandage packs. In some embodiments, each bandage pack comprises a rigid cover and a plurality of individually wrapped bandages, wherein the individually wrapped bandages are bound to each other and to the cover, wherein removal of an individual bandage from the pack causes the bound portion of the wrapper to be retained, thus freeing and partially exposing a bandage. In some embodiments, the individually wrapped bandages are bound to each other and to the cover along a bottom edge. In some embodiments, each bandage pack comprises 3 to 50 individually wrapped bandages. In further embodiments, each bandage pack comprises 5 to 40 individually wrapped bandages. In still further embodiments, each bandage pack comprises 10 to 20 individually wrapped bandages. In some embodiments, the bandage packs are the same size. In other embodiments, the bandage packs are not the same size. In some embodiments, the bandage packs have sizes selected from: 72 mm wide×40 mm deep×107 mm long, 62 mm wide×40 mm deep×107 mm long, 60 mm wide×40 mm deep×107 mm long, 80 mm wide×27 mm deep×107 mm long, 80 mm wide×34 mm deep×107 mm long, and 80 mm wide×40 mm deep×107 mm long. In some embodiments, the individually wrapped bandages have sizes selected from: 45 mm×51 mm, 40 mm×10 mm, 76 mm×38 mm, 76 mm×25 mm, and 76 mm×19 mm.

In some embodiments, the interior compartment of the dispenser body is box-shaped. In some embodiments, the lid of the dispenser body is hinged. In some embodiments, the lid is at least partially transparent. In some embodiments, the lid is made of paper or plastic. In some embodiments, the front wall of the dispenser body is at least partially transparent. In some embodiments, the dispenser body is made of paper or plastic. In some embodiments, a retaining clip is made of plastic or metal.

In another aspect, disclosed herein are systems for dispensing individual bandages comprising: a dispenser body defining a box-shaped interior compartment with an open top and comprising: a front wall, a lid that reversibly covers the open top of the interior compartment; and at least one planar divider disposed in said interior compartment perpendicular to said front wall; a plurality of bandage packs disposed in said divided interior compartment, wherein each said bandage pack comprises a rigid cover and a plurality of individually wrapped bandages, wherein said individually wrapped bandages are bound to each other and to said cover, wherein removal of an individual bandage from said pack causes the bound portion of the wrapper to be retained, thus freeing and partially exposing said bandage; and a plurality of retaining clips, wherein each clip is adapted to fit over the upper edge of said front wall, wherein each said retaining clip reversibly interlocks with said dispenser body so as to interfere with removal of a bandage pack, but allow removal of individual bandages from the interior compartment through the open top of said dispenser body.

In yet another aspect, disclosed herein are retaining clips for a bandage dispenser, wherein said bandage dispenser comprises: a dispenser body defining an interior compartment with an open or partially open top and comprising a front wall with an exposed upper edge and at least one interior compartment divider; wherein said interior compartment of said dispenser body is adapted to contain a plurality of bandage packs, wherein each said bandage pack comprises a plurality of individually wrapped bandages; and wherein said retaining clip retains a bandage pack in said dispenser body.

In some embodiments, the retaining clip fits over the exposed upper edge of the front wall and reversibly interlocks with the dispenser body such that it allows removal of individual bandages from said interior compartment through the top of the dispenser body, but does not allow removal of a bandage pack disposed therein. In further embodiments, the interlocking between a retaining clip and the dispenser body results from interaction of a protrusion and a recess. In still further embodiments, the protrusion is associated with the dispenser body and the recess is associated with a retaining clip. In other embodiments, the protrusion is associated with a retaining clip and the recess is associated with the dispenser body. In some embodiments, the interlocking between a retaining clip and the dispenser body results from friction. In some embodiments, a retaining clip interferes with removal of a bandage pack by fitting over the front wall of said dispenser body and a portion of a bandage pack simultaneously.

In some embodiments, a divider is planar and disposed in the interior compartment perpendicular to the front wall of the dispenser body. In some embodiments, a divider is fixed. In other embodiments, a divider is removable or repositionable. In some embodiments, the dispenser body comprises from 1 to 10 dividers. In further embodiments, the dispenser body comprises from 3 to 7 dividers. In still further embodiments, the dispenser body comprises 5 dividers.

In some embodiments, the dispenser body further comprises a rear wall with pre-drilled holes to facilitate mounting the dispenser to a fixed surface. In some embodiments, the dispenser body further comprises a rear wall with adhesive to facilitate mounting the dispenser to a fixed surface.

In some embodiments, the interior compartment of the dispenser body is adapted to contain 1-11 bandage packs. In further embodiments, the interior compartment of the dispenser body is adapted to contain 3-9 bandage packs. In still further embodiments, the interior compartment of the dispenser body is adapted to contain 6 bandage packs. In some embodiments, each bandage pack comprises a rigid cover and a plurality of individually wrapped bandages, wherein said individually wrapped bandages are bound to each other and to said cover, wherein removal of an individual bandage from said pack causes the bound portion of the wrapper to be retained, thus freeing and partially exposing said bandage. In further embodiments, the individually wrapped bandages are bound to each other and to said cover along a bottom edge. In some embodiments, each bandage pack comprises 3 to 50 individually wrapped bandages. In further embodiments, each bandage pack comprises 5 to 40 individually wrapped bandages. In still further embodiments, each bandage pack comprises 10 to 20 individually wrapped bandages. In some embodiments, the bandage packs are the same size. In other embodiments, the bandage packs are not the same size. In some embodiments, the bandage packs have sizes selected from: 72 mm wide×40 mm deep×107 mm long, 62 mm wide× 40 mm deep×107 mm long, 60 mm wide×40 mm deep×107 mm long, 80 mm wide×27 mm deep×107 mm long, 80 mm wide×34 mm deep×107 mm long, and 80 mm wide×40 mm deep×107 mm long. In some embodiments, the individually wrapped bandages have sizes selected from: 45 mm×51 mm, 40 mm×10 mm, 76 mm×38 mm, 76 mm×25 mm, and 76 mm×19 mm.

In some embodiments, the interior compartment of the dispenser body is box-shaped. In some embodiments, the lid of the dispenser body is hinged. In some embodiments, the lid comprises one or more transparent windows. In some embodiments, the lid is made of paper or plastic. In some embodiments, the front wall of the dispenser body comprises one or more transparent windows. In some embodiments, the dispenser body is made of paper or plastic. In some embodiments, a retaining clip is made of plastic or metal.

In yet another aspect, disclosed herein are retaining clips for an individual bandage dispenser, wherein said bandage dispenser comprises: a dispenser body defining a box-shaped interior compartment with an open or partially open top; a front wall with an exposed upper edge; a lid that reversibly covers the open top of the interior compartment; and at least one planar divider disposed in said interior compartment perpendicular to said front wall; wherein said divided interior compartment of said dispenser body is adapted to contain a plurality of bandage packs, wherein each said bandage pack comprises a rigid cover and a plurality of individually wrapped bandages, wherein said individually wrapped bandages are bound to each other and to said cover, wherein removal of an individual bandage from said pack causes the bound portion of the wrapper to be retained, thus freeing and partially exposing said bandage; and wherein said retaining clip is adapted to fit over said exposed upper edge of said front wall and reversibly interlock with said dispenser body so as to interfere with removal of a bandage pack, but allow removal of individual bandages from the interior compartment through the open top of said dispenser body.

DETAILED DESCRIPTION OF THE INVENTION

Many existing first aid systems do not adequately protect individual bandages from dirt, dust, and moisture and many are not appropriate for use in the home. Importantly, existing bandage dispensers fail to reliably retain a plurality of bandage packs simultaneously. Where retention fails, individual bandages are not dispensed cleanly or ready to apply to a wound. Advantages of the methods, devices, and systems for dispensing individual bandages described herein include enhanced protection for bandage packs and individual bandages, a dispenser that is appropriate for the home, and at least one retaining clip that reliably allows dispensing of ready-to-apply bandages that have not been excessively handled, yet also allows easy refilling.

Disclosed herein, in various embodiments, are systems for dispensing bandages comprising: a dispenser body defining an interior compartment with an open or partially open top and comprising a front wall with an exposed upper edge and at least one interior compartment divider; at least one bandage pack disposed in said interior compartment, wherein said bandage pack comprises at least one individually wrapped bandage; and at least one retaining clip, wherein said clip retains a bandage pack in said dispenser body.

Also disclosed herein, in various embodiments, are systems for dispensing individual bandages comprising: a dispenser body defining a box-shaped interior compartment with an open top and comprising: a front wall, a lid that reversibly covers the open top of the interior compartment; and at least one planar divider disposed in said interior compartment perpendicular to said front wall; a plurality of bandage packs disposed in said divided interior compartment, wherein each said bandage pack comprises a rigid cover and a plurality of individually wrapped bandages, wherein said individually wrapped bandages are bound to each other and to said cover, wherein removal of an individual bandage from said pack causes the bound portion of the wrapper to be retained, thus freeing and partially exposing said bandage; and a plurality of retaining clips, wherein each clip is adapted to fit over the upper edge of said front wall, wherein each said retaining clip reversibly interlocks with said dispenser body so as to interfere with removal of a bandage pack, but allow removal of individual bandages from the interior compartment through the open top of said dispenser body.

Also disclosed herein, in various embodiments, are retaining clips for a bandage dispenser, wherein said bandage dispenser comprises: a dispenser body defining an interior compartment with an open or partially open top and comprising a front wall with an exposed upper edge and at least one interior compartment divider; wherein said interior compartment of said dispenser body is adapted to contain a plurality of bandage packs, wherein each said bandage pack comprises a plurality of individually wrapped bandages; and wherein said retaining clip retains a bandage pack in said dispenser body.

Also disclosed herein, in various embodiments, are retaining clips for an individual bandage dispenser, wherein said bandage dispenser comprises: a dispenser body defining a box-shaped interior compartment with an open or partially open top; a front wall with an exposed upper edge; a lid that reversibly covers the open top of the interior compartment; and at least one planar divider disposed in said interior compartment perpendicular to said front wall; wherein said divided interior compartment of said dispenser body is adapted to contain a plurality of bandage packs, wherein each said bandage pack comprises a rigid cover and a plurality of individually wrapped bandages, wherein said individually wrapped bandages are bound to each other and to said cover, wherein removal of an individual bandage from said pack causes the bound portion of the wrapper to be retained, thus freeing and partially exposing said bandage; and wherein said retaining clip is adapted to fit over said exposed upper edge of said front wall and reversibly interlock with said dispenser body so as to interfere with removal of a bandage pack, but allow removal of individual bandages from the interior compartment through the open top of said dispenser body.

Dispenser Body

In some embodiments, the methods, devices, and systems for dispensing individual bandages include a dispenser body. In further embodiments, the dispenser body includes a front wall and a rear wall. In some embodiments, the front wall of the dispenser body includes an exposed upper edge. The term "exposed," as used herein, means not shielded or protected. In some embodiments, an upper edge is exposed such that it is available to contact other components of the systems and devices described herein. In some embodiments, an exposed upper edge is exposable, partially exposed, or reversibly exposed such that it is potentially, partially, or reversibly available to contact other components. In some embodiments, the front and rear walls are parallel to each other (see e.g., FIGS. 1, 2, and 5-9). In other embodiments, the front and rear walls are not parallel to each other. In some embodiments, the dispenser body includes two side walls. In further embodiments, the side walls are parallel to each other and perpendicular to the front wall and the rear wall (see e.g., FIGS. 1, and 5-9). In other embodiments, the side walls are not parallel to each other and not perpendicular to the front wall and the rear wall. In some embodiments, the dispenser body includes a bottom perpendicular to the front wall, the rear wall, and to both side walls. In some embodiments, the walls and bottom of the dispenser body are connected at right angles (e.g., 90 degrees). In various other embodiments, the walls and bottom of the dispenser body are connected at angles including, 70, 75, 80, 85, 90, 95, 100, 105, and 110 degrees. In some embodiments, one or more corners and/or edges of the dispenser body are sharp. In other embodiments, one or more corners and/or edges of the dispenser body are rounded (see e.g., FIGS. 1, 2, and 6-9).

In some embodiments, the top of the dispenser body is open. In further embodiments, the open top of the dispenser body provides easy and rapid access to individual bandages in the interior compartment. In some embodiments, the dispenser body is connected to a lid that reversibly covers the open top of the interior compartment. In further embodiments, a lid protects bandage packs and individual bandages in the interior compartment from dust, dirt, and moisture in the environment. In some embodiments, one lid reversibly covers the open top of the interior compartment. In various other embodiments, 2, 3, 4, 5, 6, 7, 8, 9, or 10 separate lids reversibly cover a portion of the open top of the interior compartment. In some embodiments, the dispenser body is connected to a lid by one or more hinges. In further embodiments, a hinge is, by way of non-limiting examples, a barrel hinge, a pivot hinge, and a continuous hinge. In some embodiments, a hinge is a sheet of flexible material or a scored or perforated section of the dispenser body that is flexible such that the connection allows the lid to move. In some embodiments, the dispenser body includes a feature that interlocks with a feature of a lid. In a particular embodiment, at least one protrusion (e.g., a peg) on the dispenser body interlocks with a recess (e.g., a hole) on a lid. In another particular embodiment, at least one protrusion (e.g., a peg) on a lid interlocks with a recess (e.g., a hole) on the dispenser body.

In some embodiments, the dispenser body defines an interior compartment. In further embodiments, the interior compartment is box-shaped. In still further embodiments, the interior of the dispenser body defines a rectangular box-shape. In still further embodiments, the interior of the dispenser body defines a square box-shape.

In some embodiments, the dispenser body includes at least one planar divider disposed in the interior compartment. In some embodiments, a divider is planar and disposed in the interior compartment of the dispenser body perpendicular to the front wall. In some embodiments, a divider is fixed such that it may not be removed or repositioned. In other embodiments, a divider is removable and/or repositionable. In some embodiments, a divider is positioned in the interior compartment of the dispenser body to define a space sized to accept a particular bandage pack. In various further embodiments, a divider defines a space that is 10, 15, 20, 25, 30, 35, 40, 45, 50, 55, 60, 65, 70, 75, 80, 85, 90, 95, and 100 mm wide. In some embodiments, divider defines a space that is 25 to 75 mm wide. In various embodiments, the dispenser body includes 1, 2, 3, 4, 5, 6, 7, 8, 9, and 10 dividers that divide the interior compartment of the dispenser body into 2, 3, 4, 5, 6, 7, 8, 9, 10, and 11 spaces, respectively. In some embodiments, the dispenser body includes 3 to 7 dividers. In further embodiments, the dispenser body includes 5 dividers.

In light of the disclosure provided herein, the dispenser body, and when present, dividers, and lids, are constructed from materials known to the manufacturing arts using techniques, tools, and machines known to the art. Suitable materials for the dispenser body, dividers, and lids are durable and rigid. Therefore, suitable materials include, by way of non-limiting examples, layered or corrugated paper, wood, plastic (e.g., polyethylene terephthalate, high-density polyethylene, polyvinyl chloride, polypropylene, high impact polystyrene, acrylonitrile butadiene styrene, and polyamide), metal (e.g., aluminum, steel, iron, nickel, titanium, zinc, and tin), carbon fiber, and combinations thereof. In some embodiments, the materials are opaque. In other embodiments, the materials are transparent. In some embodiments, a lid and/or the front wall of the dispenser body includes one or more transparent windows. In further embodiments, a lid and/or front wall of the dispenser body is entirely transparent. In still further embodiments, transparent components or materials allow an injured person to identify an appropriate bandage quickly; even while still approaching the dispenser or before opening a lid. In still further embodiments, transparent components or materials allow a homeowner to visually determine whether a bandage pack is missing or empty; even from a distance or when merely passing by the dispenser. In some embodiments, the dispenser body includes a rear wall with features adapted to facilitate mounting the dispenser to a fixed surface. In further embodiments, features adapted to facilitate mounting include, by way of non-limiting examples, pre-drilled holes (see e.g., FIG. 7), adhesive, hook and loop fasteners, magnets, and suction cups.

Figure 1:
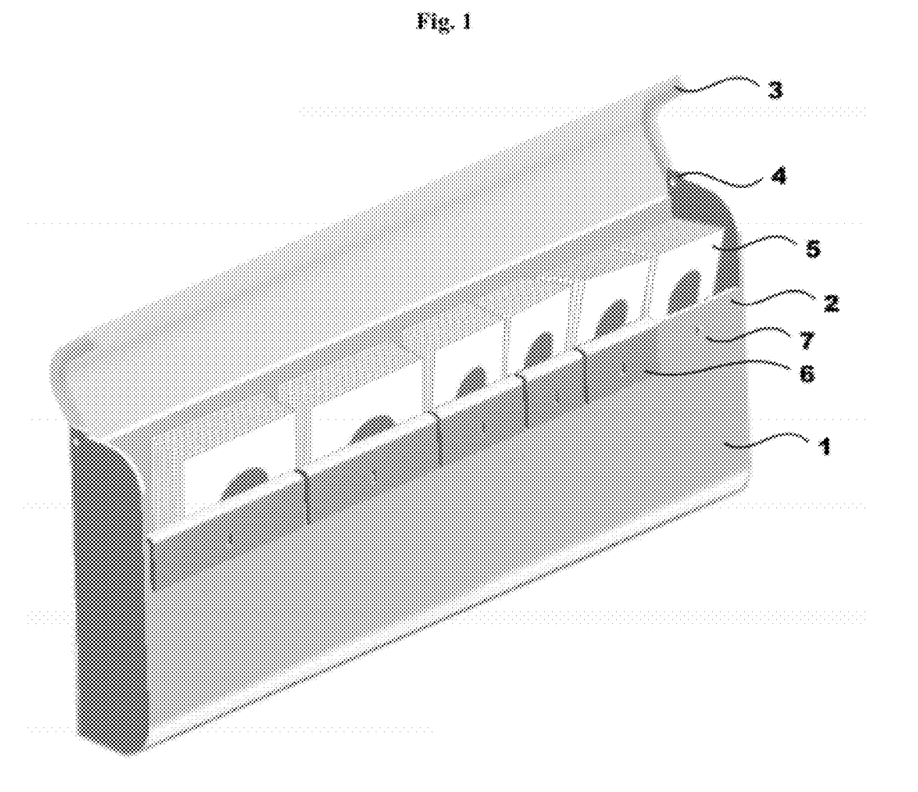
FIG. 1 shows a non-limiting example of a system for dispensing individual bandages; in this case, an assembly including a dispenser body 1, a plurality of bandage packs 5, and a plurality of retaining clips 6. The dispenser body includes an exposed upper edge 2 and is connected via a hinge 4 to a lid 3. The interior compartment of the dispenser body contains a plurality of bandage packs 5 each containing a plurality of individual bandages. A retaining clip 6 is associated with each bandage pack 5.

Referring to FIG. 1, in a particular embodiment, the dispenser body includes a front wall 1 with an exposed upper edge 2 that is parallel to a rear wall. The body has an open top that is covered by a lid 3. The lid is connected to the dispenser body by a pivot hinge 4 formed by pegs on the lid interlocking with holes on the side walls of the dispenser body.

Figure 2:
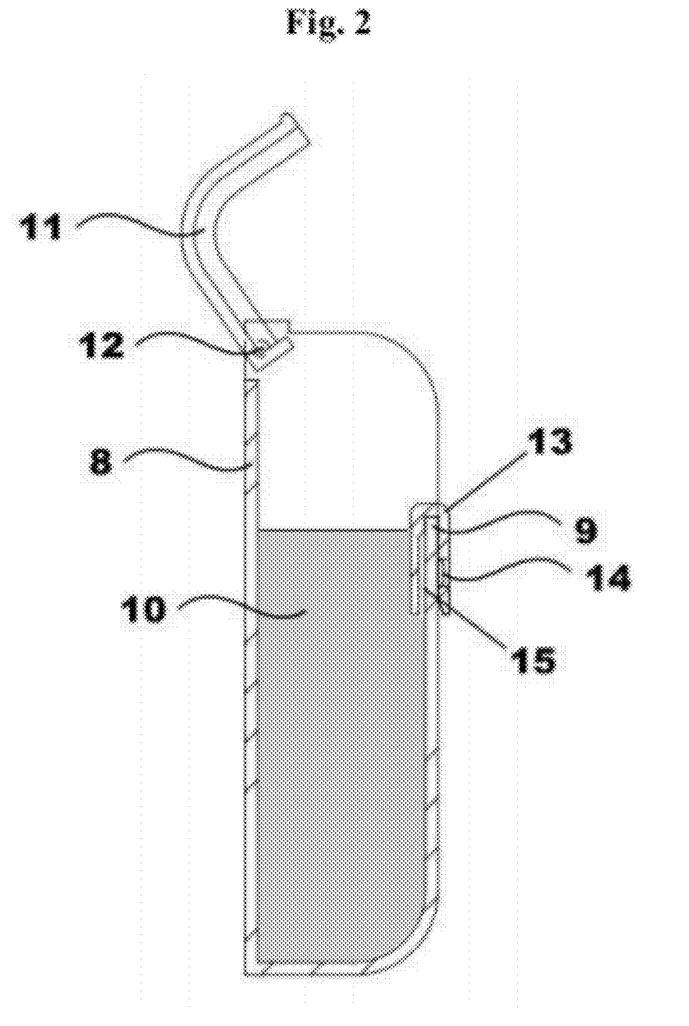
FIG. 2 shows a non-limiting example of a cross-section of an assembly for dispensing individual bandages; in this case, an assembly including a dispenser body 8 and a retaining clip 13 placed over the upper edge 9 of the dispenser body. The dispenser body 8 defines an interior compartment that is divided by at least one planar divider 10 and is connected via a hinge 12 to a lid 11. The retaining clip 13 is reversibly interlocked with the dispenser body by interaction with a protrusion 14 on the upper edge 9 of the dispenser body.

Referring to FIG. 2, in a cross-section of the particular embodiment depicted in FIG. 1, the dispenser body includes a front wall with an exposed upper edge 9 that is parallel to a rear wall 8. The body has an open top that is covered by a lid 11. The lid is connected to the dispenser body by a pivot hinge 12 formed by pegs on the lid interlocking with holes on the side walls of the dispenser body. At least one divider 10 is disposed in the interior compartment defined by the dispenser body. The dividers are perpendicular to the front wall 9 and fixed in position.

Bandage Pack

In some embodiments, the methods, devices, and systems for dispensing individual bandages includes at least one bandage pack. In various embodiments, the system includes 2, 3, 4, 5, 6, 7, 8, 9, 10, and 11 bandage packs. In further embodiments, the system includes 3-9 bandage packs. In still further embodiments, the system includes 6 bandage packs. Bandages (also referred to as adhesive bandages, sticking plasters, and plasters) are small dressings often used to cover and protect minor to moderate injuries. In some embodiments, a bandage pack includes a rigid cover that is folded to enclose a plurality of individually wrapped bandages. In further embodiments, the individual bandages extend vertically beyond the upper edge of a cover such that the individual bandages are available to grasp and remove from the pack. In some embodiments, the individually wrapped bandages are bound to each other and to the cover, such that removal of an individual bandage from the pack causes the bound portion of the wrapper to be retained, thus freeing and partially exposing a bandage for application. In further embodiments, a free, partially exposed bandage is easily and rapidly applied to an injury with one hand. In some embodiments, individually wrapped bandages are bound to each other and to the cover along a bottom edge. In further embodiments, binding is accomplished, for example, by gluing, stapling, crimping, or melting the bandage pack cover and the individual bandages along a bottom edge.

In various embodiments, each bandage pack includes 2, 3, 4, 5, 10, 15, 20, 25, 30, 35, 40, 45 and 50 individually wrapped bandages. In some embodiments, each bandage pack comprises 5 to 40 individually wrapped bandages. In further embodiments, each bandage pack comprises 10 to 20 individually wrapped bandages. In various embodiments, individual bandage are fabric bandages, plastic bandages, washproof bandages, waterproof bandages, butterfly bandages, knuckle bandages, strip bandages (e.g., rectangular), and spot bandages (e.g., circular).

In some embodiments, more than one bandage pack is disposed in the interior compartment of the dispenser body and the packs are the same size. In other embodiments, more than one bandage pack is disposed in the interior compartment of the dispenser body and the packs are not the same size. In various embodiments, a bandage pack is 10, 15, 20, 25, 30, 35, 40, 45, 50, 55, 60, 65, 70, 75, 80, 85, 90, 95, and 100 mm wide. In various embodiments, a bandage pack is 75, 80, 85, 90, 95, 100, 105, 110, 115, 120, and 125 mm high. In various embodiments, a bandage pack is 5, 10, 15, 20, 25, 30, 35, 40, 45, 50, 55, 60, 65, 70, 75, and 80 mm deep. In further embodiments, a bandage pack has dimensions selected from: 72 mm wide×40 mm deep×107 mm long, 62 mm wide×40 mm deep×107 mm long, 60 mm wide×40 mm deep×107 mm long, 80 mm wide×27 mm deep×107 mm long, 80 mm wide× 34 mm deep×107 mm long, and 80 mm wide×40 mm deep× 107 mm long. In some embodiments, the individually wrapped bandages have sizes selected from: 45 mm×51 mm, 40 mm×10 mm, 76 mm×38 mm, 76 mm×25 mm, and 76 mm×19 mm.

In light of the disclosure provided herein, a bandage pack and individually wrapped bandages are constructed from materials known to the manufacturing arts using techniques, tools, and machines known to the art. Suitable materials for a bandage pack cover include, by way of non-limiting examples, paper, cardstock, corrugated paper, and plastic (e.g., polyethylene terephthalate, high-density polyethylene, polyvinyl chloride, polypropylene, high impact polystyrene, acrylonitrile butadiene styrene, and polyamide). Suitable materials for a bandage are non-irritating, durable, and flexible and include, by way of non-limiting examples, textiles of natural fiber (e.g., cotton, linen, and hemp), textiles of synthetic fiber (e.g., nylon, polyester, aramid, olefin, and acrylic), and plastic (e.g., polyvinyl chloride, low-density polyethylene, and polypropylene). Suitable materials for a bandage wrapper are easily torn and include, by way of non-limiting examples, paper and waxed paper.

Figure 3:
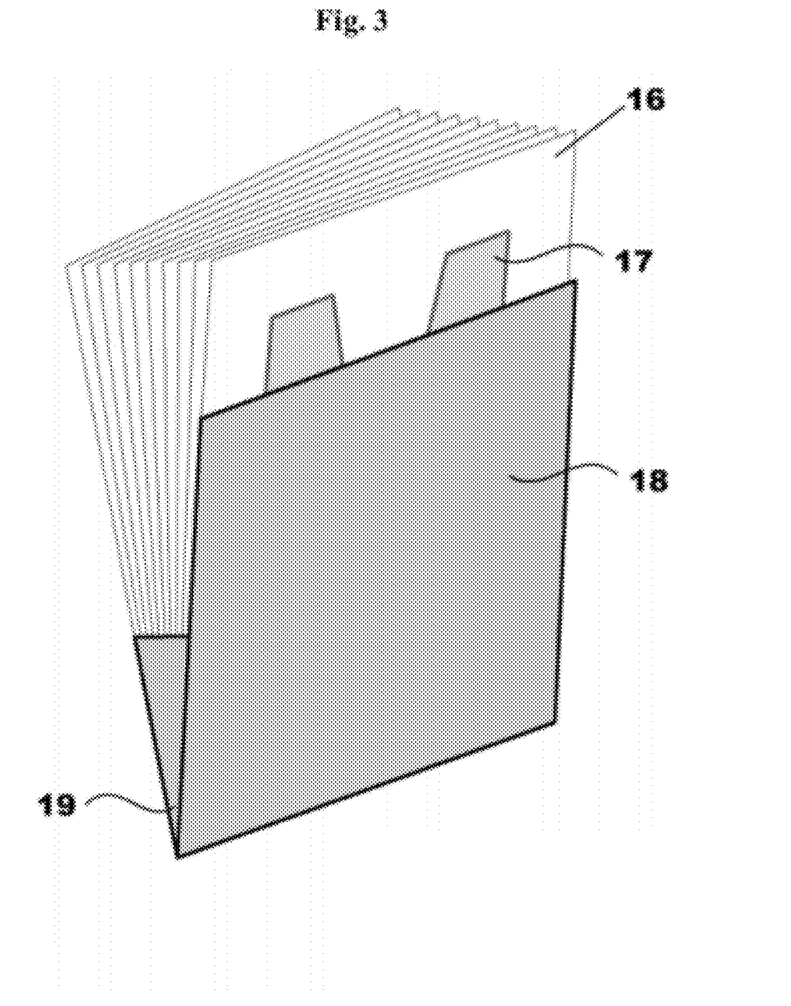
FIG. 3 shows a non-limiting example of a bandage pack; in this case, a bandage pack including a rigid cover 18 and a plurality of individually wrapped bandages 16. The bandages are bound to each other and to the cover along a bottom edge 19.

Referring to FIG. 3, in a particular embodiment, a bandage pack includes a cardstock cover 18 that is folded along a bottom edge 19 to enclose a plurality of individually wrapped knuckle bandages 16, 17. The bandage wrapper 16 includes transparent material such that the individual bandage 17 is visible through the wrapper.

Figure 4:
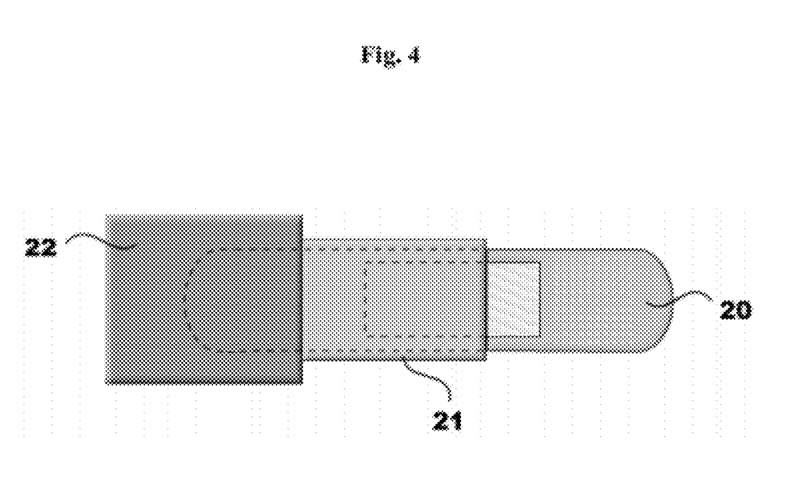
FIG. 4 shows a non-limiting example of an individually wrapped bandage; in this case, a bandage that has been removed from a bandage pack such as the example depicted in FIG. 3. Part of the wrapper 21 is retained in the bandage pack, thus partially exposing the bandage 20.

Referring to FIG. 4, in a particular embodiment, a strip bandage 20 is freed from a bandage pack and the bound portion of the wrapper is retained in the bandage pack such that only an unbound portion of the wrapper 21, 22 is associated with the bandage. In this freed and partially exposed state, the bandage 20 is available for easy and rapid application with one hand.

Retaining Clip

In some embodiments, the methods, devices, and systems for dispensing individual bandages includes at least one retaining clip. In some embodiments, a retaining clip includes 3 sides forming a channel adapted to fit over the exposed upper edge of the front wall of a dispenser body. In various embodiments, the system includes 1, 2, 3, 4, 5, 6, 7, 8, 9, 10, and 11 retaining clips. In some embodiments, the system includes 6 retaining clips. In some embodiments, the system includes one retaining clip for each division of the interior compartment of the dispenser body created by one or more dividers. In some embodiments, the system includes more than one retaining clip and the clips are one size. In other embodiments, the system includes more than one retaining clip and the clips are more than one size. In other embodiments, the system includes more than one retaining clip and the clips are various sizes. In further embodiments, the clips are sized to match divisions of the interior compartment of the dispenser body created by one or more dividers.

In some embodiments, a retaining clip reversibly interlocks with the dispenser body such that under normal conditions of use, it is only removed deliberately. In further embodiments, the interlocking between a retaining clip and the dispenser body results from interaction of at least one protrusion and at least one recess (e.g., at least one male/female interaction). In some embodiments, a protrusion is associated with the dispenser body and a corresponding recess is associated with a retaining clip. In other embodiments, a protrusion is associated with a retaining clip and a corresponding recess is associated with the dispenser body. In some embodiments, the interlocking between a retaining clip and the dispenser body results from interaction of one protrusion and one recess. In other embodiments, the interlocking between a retaining clip and the dispenser body results from interaction of a plurality of protrusions and recesses. In further embodiments, the interlocking between a retaining clip and the dispenser body results from interaction of 2, 3, 4, 5, 6, 7, 8, 9, or 10 protrusions and corresponding recesses.

In various embodiments, a protrusion has a shape selected from substantially: round, oval, oblong, triangular, square, rectangular, quadrilateral, rhomboidal, trapezoidal, pentagonal, and hexagonal. In further embodiments, a recess (e.g., a hole) corresponds to a protrusion and has a shape corresponding to the shape of a protrusion. In some embodiments, a protrusion and corresponding recess have a length-to-width ratio of greater than one and are positioned horizontally relative to the dispenser body or substantially horizontally relative to the dispenser body. In other embodiments, a protrusion and corresponding recess have a length-to-width ratio of greater than one and are positioned vertically relative to the dispenser body or substantially vertically relative to the dispenser body. In other embodiments, a protrusion and corresponding recess have a length-to-width ratio of greater than one and are positioned diagonally relative to the dispenser body or substantially diagonally relative to the dispenser body.

In some embodiments, the interlocking between a retaining clip and the dispenser body results from friction. In some embodiments, the interlocking between a retaining clip and the dispenser body results from a variation in the thickness of the front wall of the dispenser body.

In some embodiments, a retaining clip fit over, and reversibly interlocked with, the upper edge of the dispenser body interferes with removal of a bandage pack by narrowing the top opening of the dispenser body. In some embodiments, a retaining clip fit onto, and reversibly interlocked with, the upper edge of the dispenser body interferes with removal of a bandage pack by fitting over the front wall of said dispenser body and a portion of a bandage pack simultaneously. In further embodiments, the interference of a retaining clip provides a counterforce retaining a bandage pack in the interior compartment of the dispenser body when an individual bandage associated with the bandage pack is grasped and pulled upward to release it from the pack via the top opening of the dispenser body.

In light of the disclosure provided herein, retaining clips are constructed from materials known to the manufacturing arts using techniques, tools, and machines known to the art. Suitable materials for retaining clips are durable and rigid, yet offer a low to moderate degree of flexibility. Therefore, suitable materials include, by way of non-limiting examples, paper, wood, plastic (e.g., polyethylene terephthalate, high-density polyethylene, polyvinyl chloride, polypropylene, high impact polystyrene, acrylonitrile butadiene styrene, and polyamide), metal (e.g., steel, aluminum, and aluminum alloys), carbon fiber, and combinations thereof. The strength of the interlock between a retaining clip and the dispenser body is varied by selecting appropriate materials, number of interacting elements (e.g., protrusions and corresponding recesses), and the size, shape, and orientation of the interacting elements.

Referring to FIG. 1, in a particular embodiment, a retaining clip 6 is fit over the upper edge 2 of the front wall 1 of the dispenser body. A vertical, oblong protrusion 7 on the front wall reversibly interlocks with a corresponding hole in the retaining clip. In the fit and reversibly interlocked position, the retaining clip interferes with removal of a bandage pack 5 from the interior compartment of the dispenser body.

Referring to FIG. 2, in a cross-section of the particular embodiment depicted in FIG. 1, the retaining clip 13 is fit over the upper edge of the front wall 9 of the dispenser body and between the dividers 10 in the interior compartment. A protrusion 14 on the front surface of the front wall 9 of the dispenser body reversibly interlocks with a corresponding hole in the retaining clip. Further, a notch 15 evacuated from the channel of the retaining clip creates a thin space to accommodate an aspect of a bandage pack. When an aspect of a bandage pack, such as a rigid paper cover, is secured in the notch 15 in the channel of the retaining clip, the bandage pack is effectively retained in interior compartment of the dispenser body.

Figure 5:
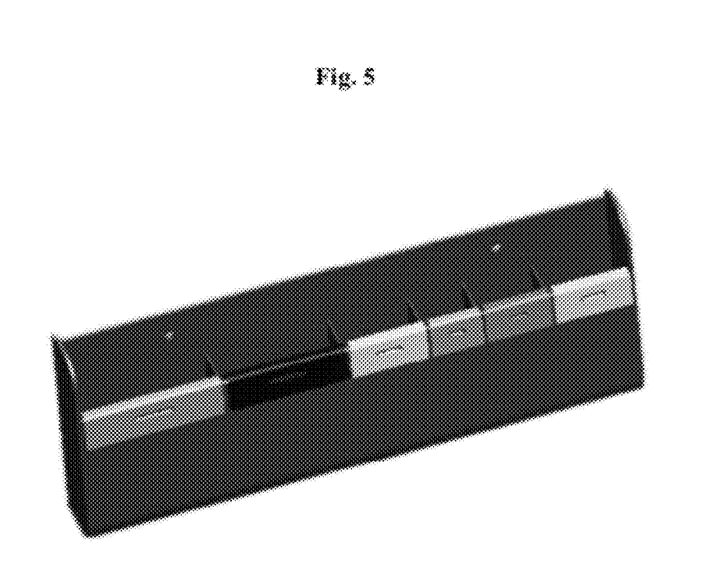
FIG. 5 shows a non-limiting example of a dispenser body; in this case, a dispenser body including five interior compartment dividers and six retaining clips fit over the upper edge of the front wall.
Figure 6:
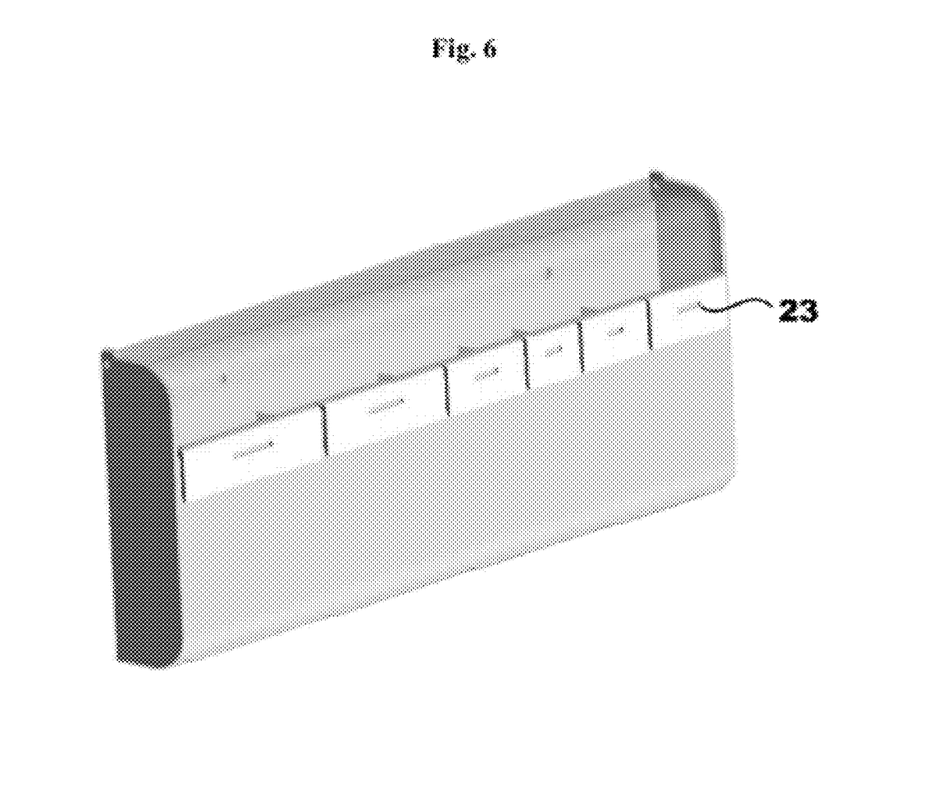
FIG. 6 shows another non-limiting example of a dispenser body; in this case, a dispenser body including a transparent lid, five interior compartment dividers, and six retaining clips fit over the upper edge of the front wall. The retaining clips reversibly interlock with the dispenser body by interaction of a protrusion on the dispenser body and a corresponding hole in the retaining clip 23.
Figure 7:
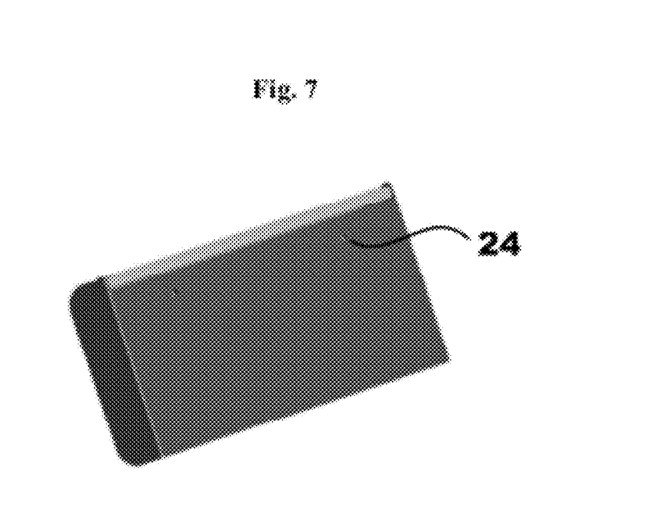
FIG. 7 shows a non-limiting example of a view of a dispenser body; in this case, a rear view of a dispenser body showing two pre-drilled mounting holes in the rear wall 24.
Figure 8:
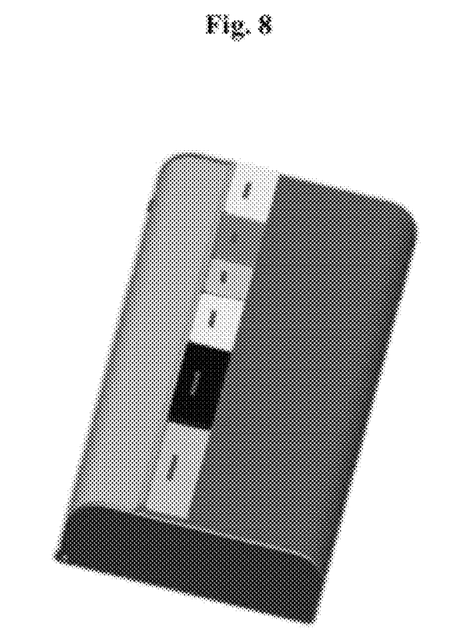
FIGS. 8 and 9 show non-limiting views of a dispenser body; in this case, views showing a dispenser body with an opaque lid and six retaining clips fit over the upper edge of the front wall.
Figure 9:
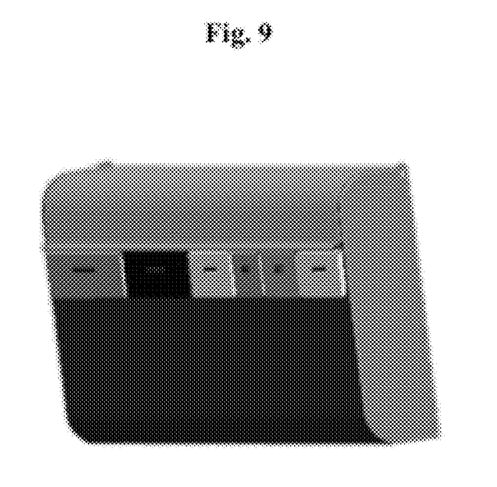

Referring to FIGS. 5 and 6, in particular embodiments, retaining clips are fit over the upper edge of the front wall of the dispenser body. One clip is associated with each division of the interior compartment of the dispenser body. One horizontal, oblong protrusion on the front wall reversibly interlocks with a corresponding hole in each retaining clip.

EXAMPLES

The following illustrative examples are representative of embodiments of the methods, devices, and systems for dispensing individual bandages described herein and are not meant to be limiting in any way.

Example 1

A 16-year-old boy is cutting a bagel in the kitchen of his home. He accidentally nicks the side of the index finger of his left hand. While the cut is only 1 cm long and 2 mm deep, he begins bleeding quite a bit and becomes alarmed. After washing the wound with clean water he realizes that he should cover the wound to protect it and to help quell the bleeding. He remembers the bandage dispenser that his father mounted to the door of the kitchen pantry. The bandage dispenser body is made of ABS plastic and is mounted to the door with double-sided adhesive tape. As the boy approaches the dispenser he can see through the transparent lid and realizes that the dispenser is stocked with bandage packs containing six sizes of bandages.

With his uninjured hand, he flips the hinged lid of the dispenser up and grasps the available end of an appropriately-sized bandage. Pulling upward on the individual bandage, its perforated wrapper gives way and he removes a partially exposed bandage through the open top of the dispenser body while the bandage pack, including a portion of the bandage's wrapper, is retained in the dispenser. The boy gently applies the bandage to his injured finger and applies light pressure to his covered wound.

Example 2

Referring to the family described in Example 1, the day after the boy is injured, his mother decides to check the bandage dispenser's supply of bandages. She surveys the six bandage packs and discovers that there is only one individually wrapped bandage left in the bandage pack offering 76×25 mm strip bandages. She decides to replace the bandage pack, exchanging with a new one. She pulls upward on a three-sided plastic retaining clip that is fit over the upper edge of the front wall of the dispenser body to release the depleted bandage pack. The clip is interlocked with the dispenser body by interaction between a 1 mm×5 mm protrusion on the dispenser body and a similarly shaped hole in the retaining clip; however, her upward pressure releases the clip from the dispenser body and frees the paper and cardstock bandage pack. After replacing the pack, she re-affixes the clip by placing it over the edge of the body and pushing downward until it snaps in place. The channel formed by the clip encompasses both the upper edge of the front wall of the dispenser and the cardstock cover of the bandage pack, thus holding the pack firmly and reliably in place.

What is claimed is:

1. A system for dispensing bandages comprising:
   a. a dispenser body defining an interior compartment with an open or partially open top and comprising a front wall with an exposed upper edge and an interior compartment divider;
   b. a bandage pack disposed in the interior compartment, wherein the bandage pack comprises at least one individually wrapped bandage; and
   c. a removable retaining clip comprising: a first wall, a second wall substantially parallel to the first wall, a third wall, and an interlocking element, wherein the first, second, and third walls form a channel adapted to reversibly interlock with the exposed upper edge of the front wall so that the retaining clip will retain a bandage pack in the dispenser body.

2. The system of claim 1, wherein the retaining clip, when interlocked with the upper edge of the front wall, allows removal of individual bandages from the interior compartment through the top of the dispenser body, but does not allow removal of a bandage pack disposed therein.

3. The system of claim 2, wherein the retaining clip reversibly interlocks with the dispenser body via interaction of a protrusion and a recess.

4. The system of claim 2, wherein the retaining clip interferes with removal of a bandage pack by fitting over the front wall of the dispenser body and a portion of the bandage pack simultaneously.

5. The system of claim 1, comprising one through eleven retaining clips.

6. The system of claim 5, comprising six retaining clips.

7. The system of claim 1, wherein the interior compartment divider is fixed.

8. The system of claim 1, wherein the interior compartment divider is removable or repositionable.

9. The system of claim 1, wherein the dispenser body comprises from one through ten dividers.

10. The system of claim 9, wherein the dispenser body comprises five dividers.

11. The system of claim 1, wherein the interior compartment divider creates a plurality of interior compartment divisions and the system comprises one bandage pack for each interior compartment division and one retaining clip for each bandage pack.

12. The system of claim 1, comprising one through eleven bandage packs.

13. The system of claim 12, comprising six bandage packs.

14. The system of claim 1, wherein the bandage pack comprises three through fifty individually wrapped bandages.

15. The system of claim 1, wherein the interior compartment is box-shaped.

16. The system of claim 1, wherein the dispenser body further comprises a lid.

17. The system of claim 16, wherein the lid is at least partially transparent.

18. The system of claim 1, wherein the front wall is at least partially transparent.

19. A system for dispensing individual bandages comprising:
   a. a dispenser body defining a box-shaped interior compartment with an open top and comprising: a front wall with an exposed upper edge, a lid that reversibly covers the open top of the interior compartment; and at least one planar divider disposed in said interior compartment perpendicular to the front wall;
   b. a plurality of bandage packs disposed in the interior compartment, wherein each bandage pack comprises a rigid cover and a plurality of bandages, wherein each bandage comprises a wrapper and is individually wrapped, wherein the bandages are bound to each other and to the cover, wherein removal of an individual bandage from a bandage pack causes the bound portion of the wrapper to be retained, thus freeing and partially exposing said bandage; and
   c. a plurality of retaining clips, wherein each retaining clip is adapted to fit over the exposed upper edge of the front wall, wherein each said retaining clip reversibly interlocks with the dispenser body so as to position each retaining clip to interfere with removal of a bandage pack, but allow removal of individual bandages from the interior compartment through the open top of the dispenser body.

* * * * *